US011721418B2

(12) United States Patent
Casse

(10) Patent No.: US 11,721,418 B2
(45) Date of Patent: *Aug. 8, 2023

(54) METHOD AND SYSTEM FOR ACCESSING CENTRALIZED PATIENT DATA

(71) Applicant: Fisher & Paykel Healthcare Limited, Auckland (NZ)

(72) Inventor: Benjamin Wilson Casse, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 88 days.

This patent is subject to a terminal disclaimer.

(21) Appl. No.: 17/302,969

(22) Filed: May 17, 2021

(65) Prior Publication Data

US 2021/0375410 A1 Dec. 2, 2021

Related U.S. Application Data

(63) Continuation of application No. 16/298,856, filed on Mar. 11, 2019, now Pat. No. 11,037,663, which is a continuation of application No. 14/647,064, filed as application No. PCT/IB2013/060393 on Nov. 26, 2013, now Pat. No. 10,255,455.

(60) Provisional application No. 61/729,756, filed on Nov. 26, 2012.

(51) Int. Cl.
*G16H 10/60* (2018.01)
*G06Q 10/10* (2023.01)
*G06F 21/62* (2013.01)

(52) U.S. Cl.
CPC ......... *G16H 10/60* (2018.01); *G06F 21/6245* (2013.01); *G06Q 10/10* (2013.01)

(58) Field of Classification Search
None
See application file for complete search history.

(56) References Cited

U.S. PATENT DOCUMENTS

| | | | |
|---|---|---|---|
| 7,181,017 B1 * | 2/2007 | Nagel | H04L 9/0841 380/282 |
| 11,037,663 B2 | 6/2021 | Casse | |
| 2002/0022973 A1 | 2/2002 | Sun et al. | |
| 2003/0212707 A1 * | 11/2003 | Uber | G16H 30/20 |
| 2006/0004588 A1 | 1/2006 | Ananda | |
| 2006/0265508 A1 * | 11/2006 | Angel | H04L 61/2567 709/230 |
| 2007/0006322 A1 | 1/2007 | Karimzadeh et al. | |
| 2008/0126729 A1 * | 5/2008 | Cai | G06Q 10/10 707/999.009 |
| 2010/0241595 A1 * | 9/2010 | Felsher | G16H 10/65 707/E17.014 |
| 2011/0110568 A1 * | 5/2011 | Vesper | G16H 30/20 382/128 |

(Continued)

FOREIGN PATENT DOCUMENTS

WO  WO 2011/019389  2/2011

*Primary Examiner* — Brandon Hoffman
(74) *Attorney, Agent, or Firm* — Knobbe, Martens, Olson & Bear, LLP

(57) ABSTRACT

A system and method is provided to allow access to centralized patient data captured from a medical device across an open network to a third party. The system and method receives the request based upon patient-specific information, checks the request and allows access if the request matches stored information.

20 Claims, 6 Drawing Sheets

(56) References Cited

U.S. PATENT DOCUMENTS

2011/0145894 A1\* 6/2011 Garcia Morchon .. H04L 63/062
726/4
2011/0313792 A1 12/2011 Mault
2013/0179176 A1\* 7/2013 Gotthardt ............... G16H 40/67
705/2
2014/0123292 A1\* 5/2014 Schmidt ................. H04L 67/10
726/25

\* cited by examiner

| Session Date / Time | usage time (hh:mm) | Compliance time | AI | HI | 90th percentile pressure | average pressure | 90th percentile leak | average leak | awakenings |
|---|---|---|---|---|---|---|---|---|---|
| Session #1 1/1/2011 10:54:00 | 5:50 | 4:15 | 5 | 7 | 12.0 | 10.0 | 40 | 30 | 5 |

| Sample | Pressure | Leak | Apnea event | Hypopnea Event | Flow limitation event | Awakening |
|---|---|---|---|---|---|---|
| 2 minutes | 10 | 43 | 1 | 0 | 0 | 0 |
| | | | 1 | 0 | 0 | 0 |
| | | | 0 | 0 | 0 | 0 |
| | | | 0 | 0 | 0 | 0 |
| | | | 0 | 0 | 0 | 1 |
| 4 minutes | 10.2 | 44 | | | | |
| 6 minutes | 10.1 | 43 | | | | |
| 8 minutes | 10.2 | 42 | | | | |

FIGURE 2

METHOD AND SYSTEM FOR ACCESSING CENTRALIZED PATIENT DATA

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to a method and system for accessing centralized patient data over an open network that has been captured from a patient, for example by a medical device.

Description of the Related Art

Medical data relating to patients is frequently captured and stored for the purposes of monitoring patients' health and assisting with their healthcare. Often, such data is captured from a medical device that the patient is using, or that is otherwise being operated to monitor or assist the patient.

An example of such a medical device is a breathing assistance apparatus. Breathing assistance apparatus are used for a variety of purposes, including PAP, oxygen treatment and the like. When using such apparatus to treat a condition, it is important that the patient complies with the treatment prescription provided by their healthcare professional. If they do not comply with the treatment prescription (such as not using the apparatus in accordance with the healthcare professionals direction) then the treatment may not be successful. Compliance of the patient to their prescription is of interest to insurance providers who fund the apparatus and treatment, and also the dealers who provide the apparatus to patients. Breathing apparatus can record compliance data for analysis so that patient compliance can be monitored and actions taken if necessary. The compliance data is normally obtained from sensors and other processors in the apparatus itself. Other information can also be captured more generally relating to medical apparatus usage and also therapy and physiology of the patient.

Various interested parties may wish to access that information. Those parties can be for example, one or more of a patient, healthcare professional, dealer, insurance provider or other interested party.

SUMMARY OF THE INVENTION

It is an object of the present invention to provide a method and system that allows access to patient data.

In one aspect the present invention may be said to consist in a method for allowing access to centralized patient data captured from a medical device across an open network to a third party comprising: receiving a request from a interested party to access centralized patient data for a patient, the request comprising request access information based on identification information associated with a patient, wherein the third party is privy to the identification information, checking that the request access information corresponds to stored access information associated with the patient, allowing the third party access to the centralized patient data for the patient if the request access information corresponds to the stored access information.

Preferably the stored access information associated with the patient is based on identification information associated with the patient.

Preferably the identification information associated with the patient comprises one or more of the following identification items: date of birth; name; medical apparatus ID; address or other contact details; social security number; or similar.

Preferably the request access information is stored or transmitted as an irreversible hash of the identification information associated with the patient.

Preferably the stored access information is created from a hash of the identification information associated with the patient.

Preferably there are different levels of access to the centralized data, each level corresponding to a different set (being all or a subset) of the (and preferably a different level of trust a party has to) the centralized patient data, and wherein allowing the third party access to the centralized patient data comprises allowing access to the set of the centralized data corresponding to an access level associated with the request access information.

Preferably the access level associated with the request access information is based on the identification items that comprise identification information.

Preferably the third party has a security level, and for one or more security levels allowing the third party access to the centralized patient data for the patient further requires receiving data from a physical key that is provided by the third party.

Preferably there are different access roles to the centralized data, each role corresponding a different level of trust a party has to the centralized patient data, and wherein allowing the third party access to the centralized patient data comprises allowing access to the set of the centralized data corresponding to the role associated with the user.

In a full trust security role a third party may be provided access to the data repository, wherein they can request data for any device, providing they provide the correct corresponding access information. Access to the repository is controlled by issuing the third party a unique key they can use to authenticate with the repository before providing device identification information and access information to access data for a specific device.

In a partial trust security role, a third party may be provided access to data for a specific device or subset of devices only my providing data contained on a physical key provided with the device, along with device identification and access information. The physical key serves as authentication, however limiting access to only the devices associated with that key.

In another aspect the present invention may be said to consist in a system for allowing access to centralized patient data captured from a medical device across an open network to a third party, the patient data being stored on a database, comprising: a computer system for: receiving a request from a third party to access centralized patient data for a patient, the request comprising request access information based on identification information associated with a patient, wherein the third party is privy to the identification information, checking that the request access information corresponds to stored access information associated with the patient, providing the third party with access to the centralized patient data in the database for the patient if the request access information corresponds to the stored access information.

Preferably the stored access information associated with the patient is based on identification information associated with the patient.

Preferably the identification information associated with the patient comprises one or more of the following identification items: date of birth; name; medical apparatus ID; address or other contact details; social security number; or similar.

Preferably the request access information is stored or transmitted as an irreversible hash of the identification information associated with the patient.

Preferably the stored access information is created from a hash of the identification information associated with the patient.

Preferably there are different levels of access to the centralized data, each level corresponding to a different set (being all or a subset) of the (and preferably a different level of trust a party has to) the centralized patient data, and wherein allowing the third party access to the centralized patient data comprises allowing access to the set of the centralized data corresponding to an access level associated with the request access information.

Preferably the access level associated with the request access information is based on the identification items that comprise identification information.

Preferably the third party has a security level, and for one or more security levels allowing the third party access to the centralized patient data for the patient further requires receiving data from a physical key that is provided by the third party.

Preferably there are different access roles to the centralized data, each role corresponding a different level of trust a party has to the centralized patient data, and wherein allowing the third party access to the centralized patient data comprises allowing access to the set of the centralized data corresponding to the role associated with the user.

In a full trust security role a third party may be provided access to the data repository, wherein they can request data for any device, providing they provide the correct corresponding access information. Access to the repository is controlled by issuing the third party a unique key they can use to authenticate with the repository before providing device identification information and access information to access data for a specific device.

In a partial trust security role, a third party may be provided access to data for a specific device or subset of devices only my providing data contained on a physical key provided with the device, along with device identification and access information. The physical key serves as authentication, however limiting access to only the devices associated with that key.

In another aspect the present invention may be said to consist in a system configured to provide access to centralized patient data captured from a medical device across an open network to a third party, comprising: at least one database with centralized patient data and stored access information associated with the patient, a computer system in communication with the database and the third party, the computer system configured to: receive a request from the third party to access the centralized patient data for a patient, the request comprising request access information based on identification information associated with a patient, wherein the third party is privy to the identification information, check that the request access information corresponds to stored access information associated with the patient, facilitate the third party to gain access to the centralized patient data in the database for the patient if the request access information corresponds to the stored access information.

It will be appreciated that while the present invention is described in relation to a breathing assistance apparatus medical device, that should not be limiting to the scope. The invention can be applied to patient data that is captured via any medical device or using any other method.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims.

The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth. The invention consists in the foregoing and also envisages constructions of which the following gives examples only.

BRIEF DESCRIPTION OF THE DRAWINGS

Preferred embodiments of the invention will now be described with reference to the following drawings, of which:

FIG. 2 is a table showing an example of data that is captured from a breathing assistance apparatus in accordance with one embodiment of the invention.

DETAILED DESCRIPTION OF THE PREFERRED EMBODIMENT

System

Figure 1:
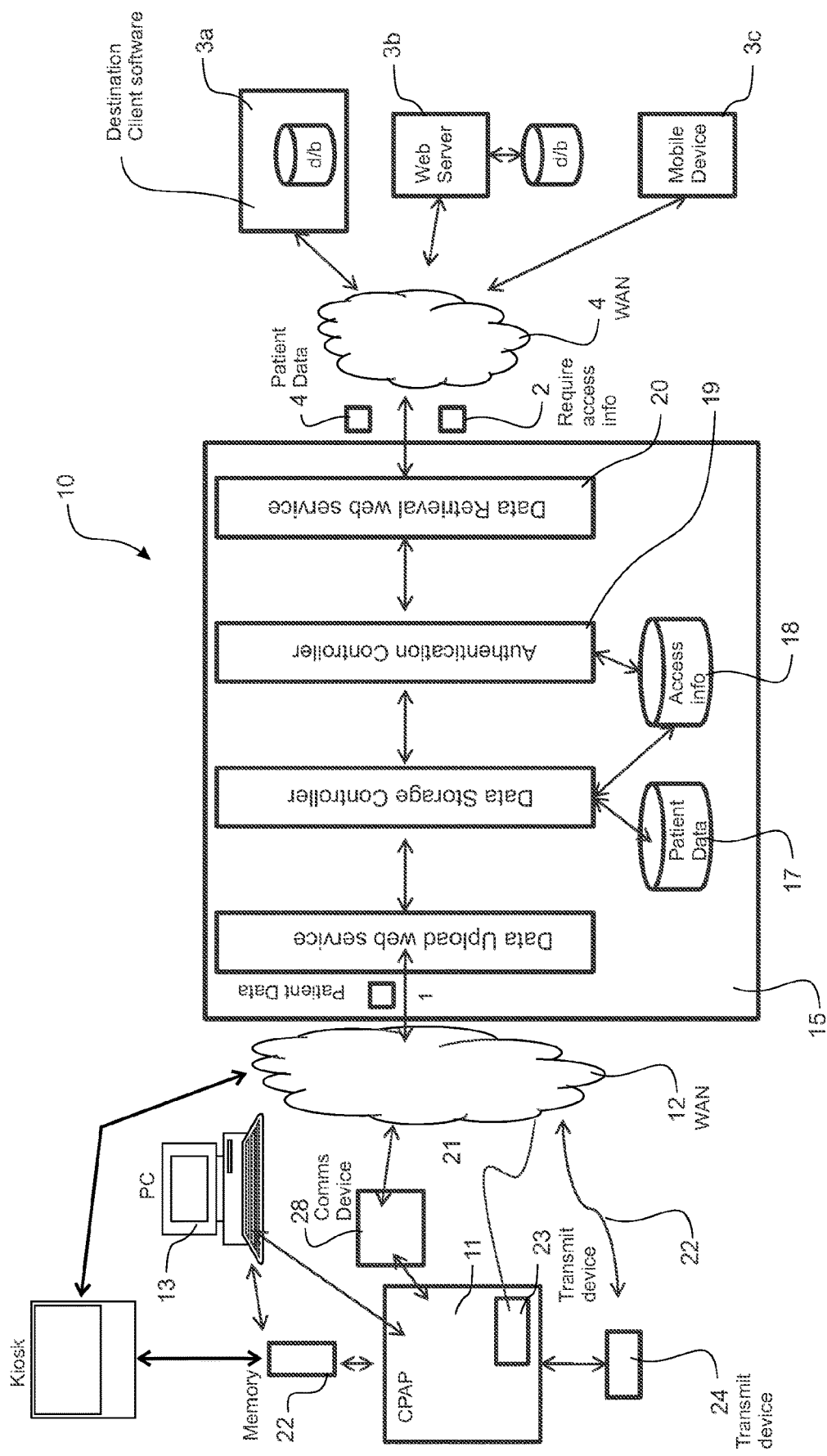
FIG. 1 is a schematic drawing of a system for capturing and storing patient data in a centralized location and allowing parties to access that data.

FIG. 1 shows a system 10 according to one embodiment that captures and stores patient data (such as medical data) in a centralized location, and allows access to that patient data by interested parties. Interested parties could be any party that may want to review patient data, such as a patient themselves, healthcare professional, dealer, insurance provider or other interested party. In this embodiment, the patient data is captured from a breathing assistance apparatus. However, it will be appreciated that more generally the patient data could be captured from any type of medical device or any other suitable method.

Each patient has a breathing assistance apparatus at their residence 11. The remaining description will refer to the breathing apparatus as a CPAP apparatus by way of example—but, this should not be considered limiting. The apparatus could be any PAP or other breathing apparatus, or other medical apparatus. The breathing assistance apparatus 11 captures patient data that is transferred for storage centrally in a database forming part of a computer system 15. The nature of the patient data that is captured and centrally stored in a database will be described later. The patient preferably will also have a computer 13, such as a PC, at their residence (or elsewhere if using e.g. GSM transmission) which is connected to a wide area network (WAN) 12, such as the internet, via a suitable connection. The CPAP apparatus 11 can be directly or indirectly in communication with the WAN 12 via a wireless or wired connection 21, 22. For example, it could be in communication with the WAN 12 via an wired or wireless external or internal modem 23, 24 or other interface using the standard telephone line or a mobile telecommunications network (such as GSM) 21, 22. In another alternative, the CPAP apparatus includes an external or internal transmission device 23, 24 for transmitting the information to the WAN 12 over a telecommunications network, such as a mobile telephone network 21, 22. Alternatively, another wireless communications system or network could be used to communicate with the WAN. This allows for transfer of the information from the CPAP machine over the WAN to the computer system 15.

Alternatively or additionally, the CPAP apparatus can be directly 25 or indirectly connected to the PC 13. This also allows for transfer of the information from the CPAP over the WAN 12 (via the PC 13) to the computer system 15. The CPAP apparatus can communicate with the PC 13 via a wired or wireless communication channel 25. Alternatively, the patient can utilize a removable memory device 27 to transfer the information between the CPAP apparatus 11 and PC 13 by physically coupling the memory device to each apparatus 11, 13 to transfer data. The PC can then transfer the information over the WAN 12 to the computer system 15, via any suitable communication network or system. It will be appreciated that the PC can instead be any computing device such as mobile computer, mobile telephone, laptop, tablet, any desktop computer, or the like.

In yet another alternative, the removable memory device 27 could be inserted into a kiosk 29 or similar, if the user is away from their home computer. The kiosk 29 is in communication with the remote computer system 15 via a telecommunications network/WAN. The kiosk is or contains a suitable computing device, such as any of those mentioned above.

In summary, any of the following modes can be used to transfer information from the CPAP apparatus 11 to the computer system 15.

GSM transmission from CPAP apparatus to remote computer system, e.g. 23 or 24, 21 or 22 or 25.

Mobile/landline telephone transmission from CPAP apparatus to PC or to remote computer system e.g. 28.

VOIP transmission, using e.g. a VOIP handset e.g. 28.

Analogue or digital telephone modem from CPAP apparatus to PC or to remote computer system e.g. 23 or 24, 21 or 22 or 25.

WIFI (or other wireless) transmission from CPAP apparatus to PC or over network to remote computer system e.g. 23 or 24, 21 or 22 or 25.

Ethernet (or other wired) transmission from CPAP apparatus to PC or over network to remote computer system e.g. 25.

Removable memory device to transfer data between CPAP apparatus and patient PC e.g. 27.

Removable memory device to transfer data between CPAP apparatus to kiosk connected to remote computer system or recipient system e.g. 27, 29.

Manual input of data displayed on CPAP apparatus into a website.

Manual/voice input of data displayed on CPAP apparatus into a mobile, landline or VOIP telephone e.g. 28.

Bluetooth™/Zigbee™ transmission from CPAP apparatus using via a home hub or other network connected device.

Bluetooth™ transmission from CPAP apparatus to mobile telecommunication device.

Data in audible form from CPAP apparatus speaker over a mobile, landline or VOIP handset/telecommunications device to the PC or remote computer system.

Figure 3:
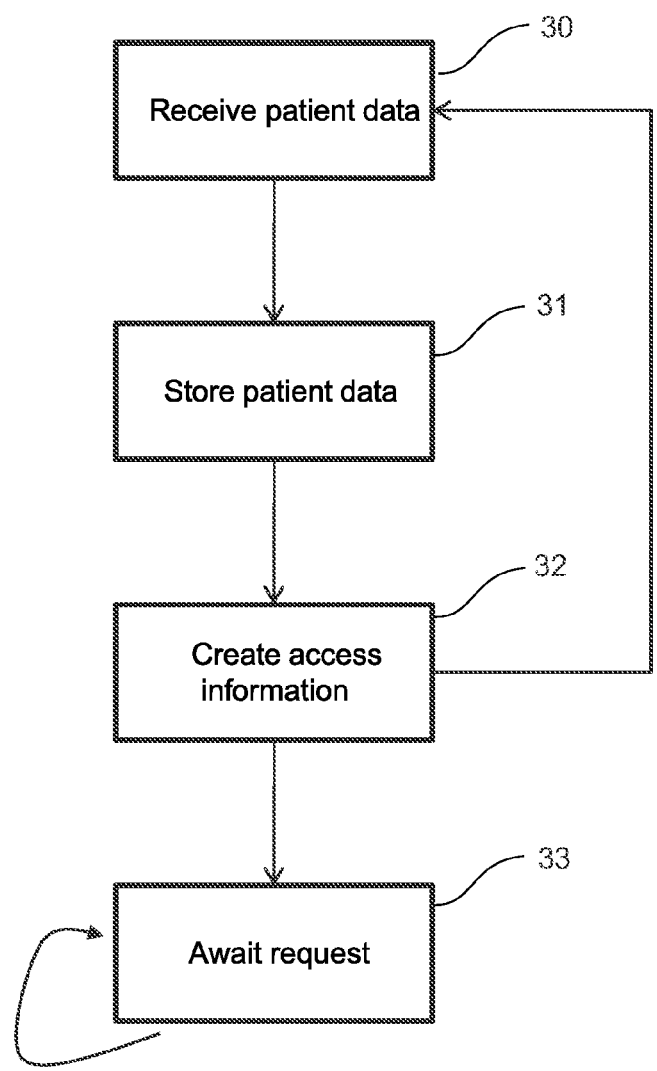
FIG. 3 is a flow diagram showing capture and storage of patient data by the system of FIG. 1.

These are just some examples of the transmissions methods, and it will be appreciated other transmission methods could be envisaged by those skilled in the art. The process of transferring patient data to the computer system 15 will be describe further in relation to FIG. 3 in the section covering the operation of the system.

The computer system 15 is connected to the WAN 12. The computer system comprises various computers, databases and other hardware components to implement the system. The hardware components can be integrated or separate, and reside in one location or alternatively distributed across multiple locations. The computer system can be operated by a single party or various independent parties, or by one or more parties under control of one or more parties. Various other options will be known to those skilled in the art.

The computer system 15 comprises a data upload Web service 14 that receives the patient data directly from the CPAP apparatus 11 over the WAN 12, or via the user PC 13, or via any other mode as previously described. For simplicity, FIG. 1 shows just a single patient medical device 11 providing data to the data upload Web service 14. However, it will be appreciated that in practice, the data upload Web service 14 will be in communication with and receive patient data from a large number of medical devices 11 used by a large number of patients distributed over a wide area. Any one of those patients and medical devices can communicate the patient data from the medical device to the Web service in any of the modes previously described as and when required to transfer patient data.

The data upload Web service 14 is in communication with a data storage controller 16. The data storage controller receives the patient data 1 and stores centrally in a patient data database 17 (centralized database). Other patient data 1 and other information obtained by alternative procedures might also be stored as patient data in the patient data database. The patient data relating to a particular patient is stored in a separate record associated with that patient (or other suitable data structure known to those skilled in the art.) The term "patient data" can refer to the patient data for multiple patients, and also to the particular patient data (and the associated record) relating to a particular patient. An example of the patient data 1 for one patient that can be captured by the CPAP apparatus 11, transferred to the computer system 15 and stored centrally as a record in the database 17 is shown in FIG. 2. It will be appreciated that this table is an illustrative example only and does not necessarily depict the data structure itself. The data will be keyed against a suitable reference (or some hash or other data derived from such a reference), such as a breathing assistance apparatus device ID (or hash or other derivative thereof). The patient data 1 will be described in further detail below with reference to FIG. 2 and the process of storing that patient data 1 will be described in more detail with reference to FIG. 3 in the section covering operation of the system.

Returning to FIG. 3, the computer system 15 also comprises a data retrieval Web service 20. This receives incoming requests 2 for patient data 1 stored centrally in the database 17 from an interested party. A request is usually received from an interested party client apparatus 3a, 3b, 3c, such as a computer 3a or mobile device 3c, over a WAN 4, such as the Internet or other open network. The computer or mobile device can be in communication with the data retrieval Web service 20 and WAN 4 by any suitable wired or wireless communications channel, such as a wired or wireless modem, mobile telecommunications connection or the like. The interested party enters the required access information (resulting in request access information 2) into a client application on their client apparatus. The request access information relates to a request for the patient data of a particular patient and comprises or is otherwise based on identification information (including device identification information) associated with a patient. The request access information (including device identification information) 2 can then be processed (if required) and passed through the WAN 4 by the telecommunications channel to the data retrieval Web service 20. Alternatively, the request 2 could be created by a destination web server 3b which upon retrieving patient data from the centralized database 17 stores it in a local database. The operation of the client apparatus 3a, 3c and client application operating thereon and the destination web server 3b will be described further with reference to FIG. 4 in the section covering operation of the system.

The computer system 15 also comprises an authentication controller 19 that communicates with the data retrieval Web service 20. The authentication controller 19 also communicates with the data storage controller 16 and allows access to the patient data 1 centrally stored in the database 17 via the data storage controller 16 if authentication is successful. The authentication controller 19 is also in communication with an access information database 18 that stores access information ("patient knowledge"). The authentication controller 19 receives the request access information 2 from the data retrieval Web service 20 from a client apparatus. The authentication controller 12 determines whether requesting (interested) party that sent the request is authorised to receive the patient data that they have requested, and if so allows the requesting party access to the patient data for that patient stored centrally in the database 17. To do this, the authentication controller checks that the request access information corresponds to one or many of (instances of) the stored access information. If it does, then the client apparatus is provided with access to the patient data on the centralized database 17 by the data storage controller 16. The client apparatus 3a, 3b, 3c is put in communication with the database 17, or receives a copy 4 of the patient data for local storage and use. This process will be described in more detail with reference to FIG. 5 in the section covering operation of the system.

Referring to FIG. 2, the patient data 1 and the manner in which it is stored centrally in the database 17 will now be described in further detail. The patient data 1 can be any medical or other related data corresponding to a patient that a third party may want to review in order to assess a patient's health and/or treatment and assist with the further treatment. Nature of patient data will be described here by way of example, although this should not be considered limiting. Patient data should be considered to comprise any data that may be associated with a patient.

As an example, patient data could be compliance, therapy and/or usage data that is recorded by the breathing assistance apparatus during use. That data relates to the use of the apparatus by the patient. The breathing apparatus may also have sensors, such as flow, pressure or physiological sensors that measure physiological parameters of the patient. The breathing assistance apparatus may also comprise a processor for processing the measurements to create further patient data. This data and the way it can be captured, recorded and processed will be known to those skilled in the art. The patient data can comprise some or all of the following: flow, mask leaks, min/max pressures, average pressures, 90th percentile pressures, AI, HI, awakenings, apnea events, hypopnea events, flow limitation events. It can also include compliance/usage data.

An example summary patient data record that is stored centrally in the database 17 is shown in FIG. 2 and replicated in the table below that includes usage time, compliance time (compliance data), AI, HI, 90th percentile pressure, average pressure, 90th percentile leak, average leak and awakenings for a usage session (efficacy data), one of these table entries is created each usage session.

TABLE 1

| Session Date/Time | usage time (hh:mm) | Compliance time | AI | HI | 90$^{th}$ percentile pressure | average pressure | 90$^{th}$ percentile leak | average leak | awakenings |
|---|---|---|---|---|---|---|---|---|---|
| Session #1 Jan. 1, 2011 10:54:00 | 5:50 | 4:15 | 5 | 7 | 12.0 | 10.0 | 40 | 30 | 5 |

An example of a detailed patient data record that is centrally stored in the database is shown below that includes, leak, pressure, apnea events, hypopnea events, flow limitation events and awakenings, one of these entries is created every two minutes within a usage session.

TABLE 2

| Sample | Pressure | Leak | Apnea event | Hypopnea Event | Flow limitation event | Awakening |
|---|---|---|---|---|---|---|
| 2 minutes | 10 | 43 | 1 | 0 | 0 | 0 |
| | | | 1 | 0 | 0 | 0 |
| | | | 0 | 0 | 0 | 0 |
| | | | 0 | 0 | 0 | 0 |
| | | | 0 | 0 | 0 | 0 |
| | | | 0 | 0 | 0 | 1 |
| 4 minutes | 10.2 | 44 | | | | |
| 6 minutes | 10.1 | 43 | | | | |
| 8 minutes | 10.2 | 42 | | | | |

The data is keyed against patient knowledge.

The access information database ("patient knowledge") 18 comprises access information that is checked against the request access information 2 provided by the interested party making the request for patient data for a particular patient. Access information is associated with each patient/patient data record in the database 17. Each patient record or patient can have one or more separate instances of patient knowledge keyed/associated with it. Any one of the instances of patient knowledge can be utilised to gain access/authorisation to review the patient record. The access information is based upon identification information associated with the respective patient. That is, identification information identifies the respective patient directly or indirectly, or has some other association with the patient (such as device identification). The access information (or identification information it is based on) is patient related information that the requesting party must know in order to send a request and access a patient data record for a particular patient on the centralized database.

A typical storage structure and relation between device data and access information is illustrated below. The data is preferably stored in a relational SQL database consisting of three tables. First, a device identity table is provided containing the device index (that is, a medical device/apparatus identification number such the serial number of the patients CPAP device).

The device identify table has a many to one relationship to two other tables, being:

a device data table that contains a row for each session of device usage data, these rows being related to a device identity by a foreign key (FK) relationship, and a patient knowledge (access information table) containing a hash coded version ("knowledge hash") of each element (identification information/items) of patient knowledge (access information) received for a particular device, these rows are related to a device identity by a foreign key relationship.

| Device Identity table | |
|---|---|
| Serial Number | Id |
| 120101000001 | 1 |
| 120101000002 | 2 |
| 120101000003 | 3 |

| Device Data Table (additional data columns may be stored | | | | | |
|---|---|---|---|---|---|
| FK_Id | Usage Date/Time | Run Hours | Comply Hours | AHI | Mask Leak |
| 1 | 1 Jan. 2012 9:00 pm | 5 | 5 | 7 | 34 |
| 1 | 2 Jan. 2012 9:34 pm | 5.2 | 5.1 | 5 | 35 |
| 2 | 1 Jan. 2012 9:22 pm | 7 | 5 | 6 | 37 |
| 2 | 2 Jan. 2012 9:43 pm | 7.7 | 6.2 | 4 | 36 |
| 2 | 3 Jan. 2012 11:12 pm | 5.6 | 5 | 6 | 32 |
| 3 | 3 Jan. 2012 10:52 pm | 8 | 5 | 6 | 33 |

| Device Access Information Table | |
|---|---|
| FK_Id | Knowledge Hash |
| 1 | 166320e78acd71b8deb63c8dfca0de04 |
| 1 | 8a50bf987eff655ca6c33e7d0542a95b |
| 2 | cd39a1073eab7dbfa1e729fd2ed1cd30 |
| 3 | 47c5de4e72ff1cf2e1aea0bc915e473f |

Access information (and/or the identification information it comprises) is information that in part or in whole would not ordinarily be known by a party unless they had some link or other authorisation with the patient thus making them privy to such information.

The identification information comprises identification items associated with the respective patient such as one or more of the following: date of birth; name; medical device ID; address or other contact details; social security number; or similar. This list is not exhaustive and any suitable identifying information could be an identification item.

The access information might comprise one or more of the identification items associated with the respective patient, or might comprise information being, derived from or otherwise related to one or more of the identification items. For example, the access information might be a collection of identification items, or a hash of one or more of the identification items. The term access information can refer to both the hashed or unhashed form of the information. In a preferred embodiment, the identification information is hashed, and the hash of that information is keyed/associated with the patient/patient record/patient information and stored in the database 18. In this case, preferably no actual identification information of a patient is stored, only derivative information (e.g. a hash) of the identification information. This increases patient security/privacy. The access information is stored as a hashed value. The information is hashed by the server before being stored if it is received in an unencrypted state. The hash is an irreversible hash algorithm such as SHA1.

Request access information is based on identification information associated with the particular patient (or patient record) relating to the request. If the hashed version of the request access information corresponds with (e.g. matches) any stored hashed access information for the same patient, then the authentication controller will allow the requesting party access to the patient data record of the associated patient.

The above description describes a system, which comprises a computer system 15, patient medical device and associated telecommunications hardware, and interested party client apparatus. All of these would typically operated by different parties that operate independently. While the system might be considered to be all aspects, it could also be considered to be just the computer system 15 that facilitates upload and storage of patient data and access to patient data by client apparatus.

Operation

Operation of the system will now be described with reference to FIGS. 3 to 6. The computer system 15 receives patient data as it is captured and recorded by a breathing assistance apparatus 11, step 30. This is received at the data upload Web service 14 from the breathing assistance apparatus 11 by any mode described with reference to FIG. 1. The patient data 1 is received from some or all of the breathing assistance apparatus that communicate with the computer system as and when such information is captured and communicated. Access information is included in the transmission of the data and is received by the data upload Web service. As the patient data 1 is received by the data upload Web service 14, it is passed to the data storage controller 16 the device data is stored in the centralized patient database 17, step 31. The access information is hashed and also stored, related to the device in the access information database 18 and keyed against the patient data as described above, step 32. The process, steps 30 to 32, occurs repeatedly as new patient data is captured and uploaded. At any point, the computer system is available and waiting to receive requests for patient data for a particular patient from a requesting party, step 33. Any particular patient data could have multiple different access information associated with it, each being created through hashing of different identification information (i.e. a different combination of identification items). This enables different parties with different knowledge about the patient to access the patient data.

Having several sets of identification information associated with patient data also enables different levels of security/access/roles. Different sets or subsets of patient data can be associated with different identification information. Where, for example, an interested party knows certain identification information of the patient, that party might have access to some subset or all of the patient data of a patient, while another party that knows other identification information might have access to different set or subset of the patient data of the same patient. Security on a patient's data can also be elevated, requiring a certain number of matching pieces of access information be provided before access is granted.

Having access to data at a full trust role might also be contingent on providing a unique key to authenticate. This might provide an added level of authorisation required for access to the patient data repository. Preferably, there will be two levels of security (although any suitable number is possible). The first level is authentication and the second level is authorisation, in that order. Preferably (although not essentially) an API key is used for authentication.

Having access to data at a partial trust role might also be contingent on providing information from a physical key 27a, such as a dongle. This might provide an added level of authorisation required to access the data associated with the dongle in place of a unique key. Such information on the physical key could be considered a part of the access information, and may itself be hashed on in its raw form.

The system then awaits an access request for patient data.

Figure 4:
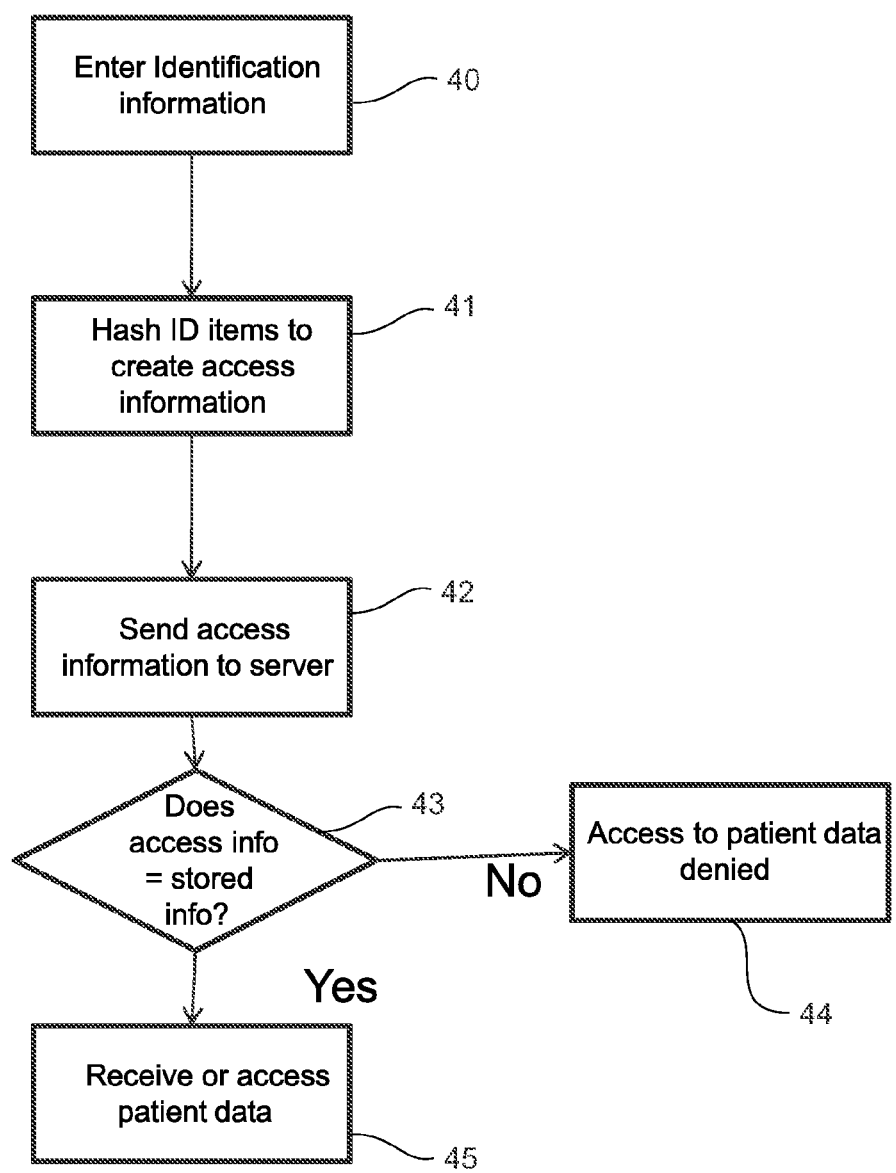
FIG. 4 is a flow diagram showing a party requesting centrally stored patient data from the system of FIG. 1.

Referring now to FIG. 4 operation of the system from the perspective of the interested party is described. When an interested party wants to request patient data from the database, they enter a request. They then become the requesting party. The request can be entered into a client application running on a client computer or on a mobile device, for example. The request comprises entering the device identification information and access information, such as the identification items associated with the patient of whom data is being requested, step 40. The server 20 or application or other computer system/service then may hash the input identification information to create the access information, step 41. This access information is then sent to the authentication controller 19, step 42. The access information is compared to the stored access information in the database 18. If there is a match, step 43, the access is provided to the patient information/data which the access information in the database 18 is associated with step 45. The requesting party is provided with or access to the relevant patient data in the database 17. This can be viewed or transferred back to the requesting party computer system. If there is not a match, step 43, the access to the requested patient data is denied, step 44.

Figure 6:
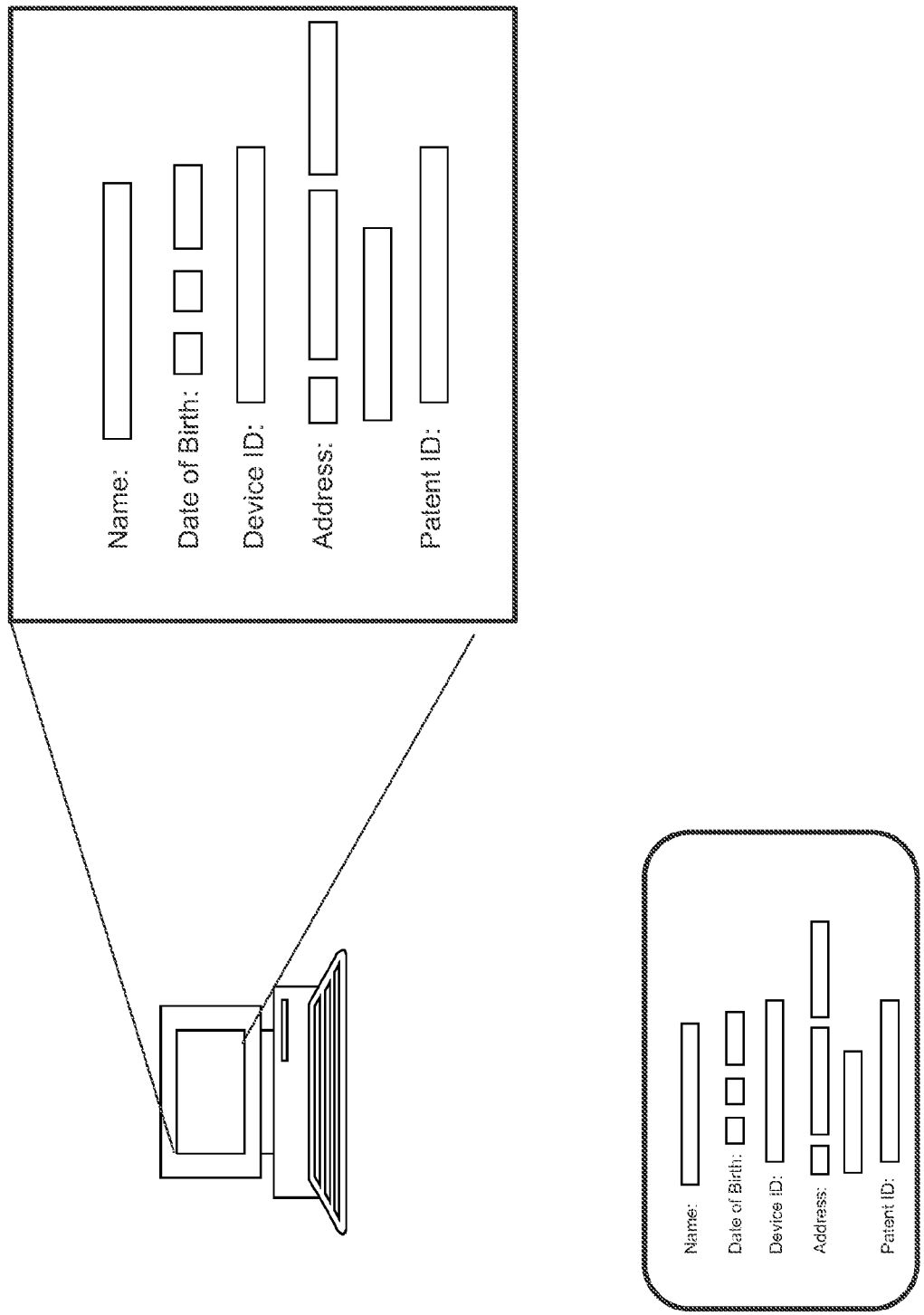
FIG. 6 shows the user interface of client software on a PC and mobile device respectively which is operated by a party to gain access to centralized patient data through the system of FIG. 1.

Referring to FIG. 6, the information for the request is entered in a graphical user interface of the client software/app.

In one embodiment, the client application processes the entered identification items to produce the access information. This could be done, for example, by creating a hash of the identification items/elements, step 41. The request, including the access information is sent to the computer system 15, where it is received by the data retrieval Web service, step 42. The request access information is forwarded to the authentication controller where it is compared with access information in the access information database step 43. If the request access information corresponds to stored access information, then the authentication controller then allows access to the patient data on the centralized database. Alternatively, the authentication controller via the data storage controller provides a copy of that patient data to the client apparatus. Alternatively, if the request access information does not match any of the stored access information on the database then no access is provided to the patient data.

Figure 5:
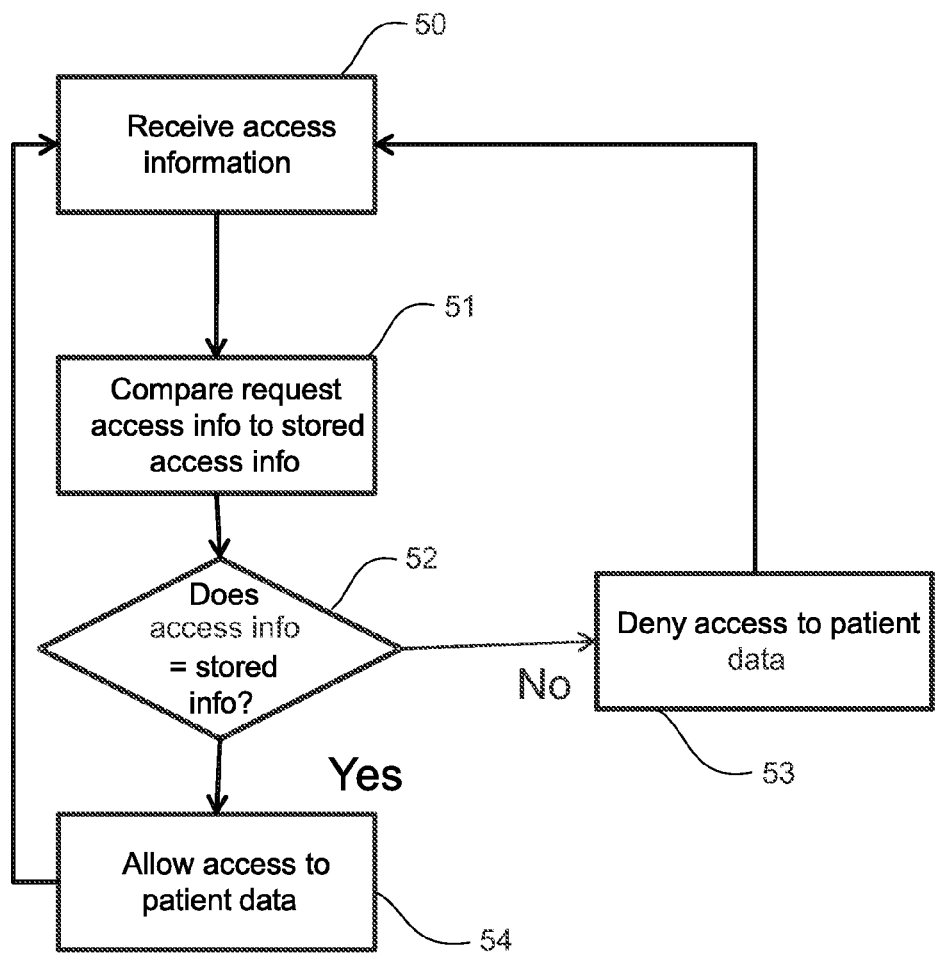
FIG. 5 is a flow diagram showing operation of the system of FIG. 1 to allow access to patient data stored in a centralized location.

Now referring to FIG. 5, operation of the system from the perspective of the system will be described. The system receives access information provided on a request from a client apparatus, step 50. The access information is received at the data retrieval Web service and passed to the authentication controller for comparison, step 51. If the request access information corresponds to stored access information, step 52, then the authentication controller then allows access to the patient data on the centralized database, step 54. Alternatively, the authentication controller via the data storage controller provides a copy of that patient data to the client apparatus. Alternatively, if the request access information does not match any of the stored access information on the database, step 54, then no access is provided to the patient data, step 53.

What is claimed is:

1. A method for allowing access to remote patient data, captured from a medical device, across an open network to a third party comprising:
   receiving a request from an interested party, via a computer device operated by the interested party, to access remote patient data for a patient over an open network stored in a remote database, the request comprising request access information based on identification information associated with a patient, wherein the third party is privy to the identification information;

hashing at least a portion of the request access information to create hashed access information;

checking that the hashed access information corresponds to stored access information associated with the patient;

allowing the third party access to the remote patient data for the patient on the database or transmitting patient data to the computer device operated by the interested party from the database if the hashed access information corresponds to the stored access information.

2. The method of claim 1, wherein the request is sent from a client application running on the computer device operated by the interested party to a server.

3. The method of claim 2, wherein the computer device is a laptop computer, desktop computer, or a mobile device.

4. The method of claim 1, wherein the request comprises device identification information.

5. The method of claim 1, wherein the hashing and checking the hashed access information is performed on a server.

6. The method of claim 1, wherein the hashing is performed by an application running on the computer device operated by the interested party.

7. The method of claim 6, wherein the checking the hashed information is performed on a server.

8. The method of claim 6, wherein the checking the hashed information is performed by the application running on the computer device associated with the interested party.

9. The method of claim 6, wherein the hashing is performed by a hashing algorithm.

10. The method of claim 6, wherein all request access information is hashed.

11. The method of claim 1, further comprising entering the access information in a graphical user interface of an application.

12. The method of claim 1, further comprising providing a different level of access based on a type of request access information provided.

13. The method of claim 12, wherein a different level of access comprises access to less than all information stored about a patient.

14. The method of claim 12, wherein a different level of access comprises access to all information stored about a patient.

15. The method of claim 12, wherein a different level of access comprises access to information relevant to the request access information provided.

16. A system configured to implement the method of claim 1.

17. A non-transitory computer-readable storage medium, the computer-readable storage medium including instructions that when executed by a computer, cause the computer to operate an application, the application performing the steps of:

receiving a request from an interested party via the application operating on a computer device associated with the interested party, wherein the request requests access to patient data of a patient over an open network stored on a remote database, the request comprising access information based on identification information associated with a patient, wherein the third party is privy to the identification information;

hash at least a portion of the request access information to create hashed access information;

transmit a modified request to access information, wherein the request is modified to comprise the hashed access information, to a server which checks that the hashed access information corresponds to stored access information associated with the patient;

receive an indication that the hashed access information has been accepted and providing access to the computer device to access the remote patient data for the patient on the database.

18. The non-transitory computer-readable storage medium of claim 17, wherein the application is further configured to receive patient data.

19. The non-transitory computer-readable storage medium of claim 17, wherein the patient data is encrypted.

20. The non-transitory computer-readable storage medium of claim 17, further comprising providing a different level of access based on a type of the hashed access information received at the server.

* * * * *